(12) United States Patent
Ma et al.

(10) Patent No.: US 7,358,729 B2
(45) Date of Patent: Apr. 15, 2008

(54) METHODS AND APPARATUSES FOR FAST CHEMICAL SHIFT MAGNETIC RESONANCE IMAGING

(75) Inventors: Jingfei Ma, Houston, TX (US); Haesun Choi, Houston, TX (US); R. Jason Stafford, Houston, TX (US); James A. Bankson, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 317 days.

(21) Appl. No.: 11/271,060

(22) Filed: Nov. 10, 2005

(65) Prior Publication Data

US 2006/0094952 A1    May 4, 2006

Related U.S. Application Data

(62) Division of application No. 10/882,111, filed on Jun. 30, 2004, now Pat. No. 7,084,626.

(51) Int. Cl.
*G01V 3/00* (2006.01)
(52) U.S. Cl. ...................... 324/307; 324/309
(58) Field of Classification Search .............. 324/307, 324/309, 312; 600/410
See application file for complete search history.

(56) References Cited

U.S. PATENT DOCUMENTS 5,995,863 A * 11/1999 Farace et al. .............. 600/410
6,208,139 B1    3/2001 Foo et al.
7,027,853 B2 * 4/2006 Ma ............................ 600/410
7,084,626 B2 * 8/2006 Ma et al. .................... 324/307
7,227,359 B2 * 6/2007 Ma ............................ 324/309

OTHER PUBLICATIONS

Ahn and Cho, "A new phase correction method in NMR imaging based on autocorrelation and histogram analysis," *IEEE Trans. Med. Imaging*, 6(1): 32-36, 1987.
Ahn et al., "Non-proton imaging and spectroscopy," *Magn. Reson. Imaging*, 4:110, 1986.
An and Xiang, "Chemical Shift imaging with spectrum modeling," *Magn. Reson. Med.*, 46(1):216-130, 2001.
An and Xiang, "Quadrature 2-point water fat imaging," *Proc. 4th Annual Scientific Meeting of the Intl Soc. for MRI in Medicine*, NY, 1541, 1996.

(Continued)

*Primary Examiner*—Louis M. Arana
(74) *Attorney, Agent, or Firm*—Bracewell & Giuliani LLP

(57) ABSTRACT

Systems and methods are described for chemical shift magnetic resonance imaging in the presence of multiple chemical species. A method includes obtaining a plurality of MRI data signals using a Dixon technique in combination with partially parallel imaging techniques and/or inversion recovery techniques, and processing the plurality of MRI data signals using a Dixon reconstruction technique to create a chemical specific shift image. An apparatus includes a MRI scanner for obtaining images, a controller configured to provide input to the scanner to acquire images using a Dixon technique in combination with partially parallel imaging techniques and/or inversion recovery techniques to produce a plurality of MRI data signals, and processing the plurality of MRI data signals using a Dixon reconstruction technique to create a chemical specific shift image, and an output device to display the resulting image.

33 Claims, 9 Drawing Sheets

OTHER PUBLICATIONS

Araki et al., "Magnetic resonance imaging of brain tumors: measurement of T1," *Radiology*, 150:95-98, 1984.

Axel, "Surface coil magnetic resonance imaging," *J. Comput. Assist. Tomogr.*, 8(3):381-384, 1984.

Bailes et al., "NMR imaging of the brain using spin-echo sequences," *Clin. Radiol.*, 33:395=-414, 1982.

Bailes et al., "Respiratory ordered phase encoding (ROPE): A method for reducing respiratory motion artifacts in MR Imaging," *J. Comput. Assist. Tomogr.*, 9(4):835-838, 1985.

Bankson et al., "Partially parallel imaging with phase-sensitive data: increased temporal resolution for MR thermometry," *Proc. Intl. Soc. Magnetic Resonance in Medicine*, Hawaii, 10:2002.

Berkel et al., "Breast augmentation: a risk factor for breast cancer?" *N. Engl. J.Med.*, 326(25):1649-1653, 1992.

Bernstein et al., "Improved detectability in low signal-to-noise ratio magnetic resonance images by means of a phase-corrected real reconstruction," *Med. Phys.*, 16(5):813, 1989.

Bilbey et al., "MR imaging of adrenal masses: value of chemical-shift for distinguishing adenomas for other tumors," *Am. J. Roentgenol.*, 164:637-642, 1995.

Borkowski et al., "Nuclear magnetic resonance (NMR) imaging in the evaluation of the liver: a preliminary experience," *J. Comput. Assist. Tomog.*, 7:768-774, 1983.

Bottomley et al., "A review of normal tissue hydrogen NMR relaxation times and relaxation mechanisms from 1-100 Nhz: dependence on tissue type, NMR frequency, temperature, species, excision, and age," *Med. Phys.*, 11(4):425-448, 1984.

Brey and Narayana, "Correction for intensity falloff in surface coil magnetic resonance imaging," *Med. Phys.*, 15(2):241-245, 1987.

Brown et al., "NMR chemical shift imaging in three dimensions," *Proc. Natl. Acad. Sci. USA*, 79:3523-3526, 1982.

Bydder and Young, "MR imaging: clinical use of the inversion recovery sequence," *J. Comput. Assist. Tomogr.*, 9(4):659-675, 1985.

Bydder et al., "Clinical NMR imaging of the brain: 140 cases," *Am. J. Roentgenol*, 139:215-236, 1982.

Bydder et al., "Use of spherical receiver coils in MR imaging of the brain," *J. Comput. Assist. Tomogr.*, 9(2):413-414, 1985.

Bydder et al., "MR imaging of memingiomas including studies with and without gadolinium-DTPA," *J. Comput. Assist. Tomogr.*, 9(4):690-697, 1985.

Carr et al., "Gadolinium DTPA as a contrast agent in MRI: initial clinical experience in 20 patients," *Am. J. Roentgenol*, 143:215-224, 1984.

Dickinson, "Dependence of the F19 nuclear resonance position on chemical compound," *Phys. Rev.*, 77:736, 1950.

Dixon, "Simple proton spectroscopic imaging," *Radiology*, 153:189-194, 1984.

Doyle et al., "Nuclear magnetic resonance imaging of the liver: initial expericence," *Am. J. Roentgenol* 138:193-200, 1982.

Droege et al., "A strategy for magnetic resonance imaging of the head: results of a semi-empirical model," *Radiology*, 153:425-433, 1984.

Gadian et al., "Gadolinium-DTPA as a contrast agent in MR imaging-theoretical projections and practical observations," *J. Comput. Assist. Tomogr.*, 9(2):242-251, 1985.

Gao et al., "Effects on selective excitation and phase uniformity of orthogonal field gradient components," *Proc. 10th Ann. Mtg. Soc. Mag. Resonance in Medicine*, San Francisco: Society of Magnetic Resonance in Medicine, 132, 1991.

Glover et al., "Three-point Dixon technique for true water/fat decomposition with $B_0$ inhomogeneity correction," *Magn. Reson. Med.*, 18:371-383, 1991.

Gorczyca et al., "Silicone breast implant rupture: comparision between three-point Dixon and fast spin-echo MR imaging," *Am. J. Roentgenol*, 162(2): p. 305-310, 1994.

Graham et al., "Changes in fibroglandular volume and water content of breast tissue during the menstrual cycle observed by MR imaging at 1.5 T," *J. Magn. Reson .Imaging*, 5:695-701, 1995.

Griswold et al., "An RF array designed for cardiac SMASH imaging," *Proc. ISMRM 6th Annual Meeting*, Sydney, 437, 1998

Hardy et al., "Separation of fat and water in fast spin-echo MR imaging with the three-point Dixon technique," *J. Magn. Reson. Imaging*, 5(2): 181-185, 1995.

Harms et al., "Silicon-suppressed 3D MRI of the breast using rotating delivery of off-resonance excitation," *J. Comput. Assist. Tomogr.*, 19(3):394-399, 1995.

Haselgrove and Prammer, "An algorithm for compensation of surface-coil images for sensitivity of the surface coil," *Magn. Reson. Imaging*, 4:469-472, 1986.

Hendrick et al., "Optimizing tissue contrast in magnetic resonance imaging," *Magn. Res. Imaging*, 2:193-204, 1984.

Henkelman et al., "Why fat is bright in RARE and fast spin-echo imaging," *J. Magn. Reson. Imaging*, 2:533-540, 1992.

Hennig et al., "RARE imaging: method for clinical MR," *Magn. Reson. Med.*, 3:823-833, 1986.

Hutchinson and Raff, "Fast MRI data acquisition using multiple detectors," *Magn. Reson. Med.*, 6:87-91, 1988.

Ikeda et al., "Silicone breast implant rupture: pitfalls of magnetic resonance imaging and relative efficacies of magnetic resonance, mammography, and ultrasound," *Plast. Reconstr. Surg.*, 104(7):2054-2062, 1999.

Jakob et al., "Auto-Smash, a self-calibrating technique for SMASH imaging," *Proc. ISMRM 6th Ann. Mtg.*, Sydney, 1975, 1998.

Jakob et al., "Cardic imaging with SMASH," *Proc. ISMRM 6th Ann. Mtg.*, Sydney, 16, 1998.

Joseph, "A spin echo chemical shift MR imaging technique," *J. Comp. Asst. Tomogr.*, 9(4):651-658, 1985.

Judge and Bryanston-Cross, "A review of phase unwrapping techniques in fringe analysis," *Optics and Lasers in Eng.*, 21:199-239, 1994.

Keller et al., "Multisection fat-water imaging with chemical shift selective presaturation," *Radiology*, 164:539-541, 1987.

Kuroda et al., "Optimization of chemical shift selective suppression of fat," *Magn. Reson. Med.*, 40:505-510, 1998.

Kurtz and Dwyer, "Isosignal contours and signal gradients as an aid to choosing MR imaging techniques," *J. Comput. Assist. Tomogr.*, 8(5):819-828, 1984.

Kwiat et al., "A decoupled coil detector array for fast image acquisition in magnetic resonance imaging," *Med. Phys.*, 18(2):251-265, 1991.

Li et al., "MR imaging in CNS tumors," *Radiology*, 153(P) 85, 1984.

Lodes et al., "Proton MR chemical shift imaging using double and triple phase contrast acquisition methods," *J. Comput. Assist Tomogr.*, 13(5):855-861, 1989.

Ma et al., "Multipoint Dixon Imaging using Sensitivity Encoding," *Proc. Intl. Soc. Magnetic Resonance in Resonance in Medicine*, Toronto, Canada, (11) 1069, 2003.

Ma et al., "Method for efficient fast spin echo Dixon imaging," *Magn. Reson. Med.*, 48(6):1021-1027, 2002.

Ma, "Multipoint Dixon imaging with reduced time and increased reliability," *Proc. 6th Ann. Mtg. ISMR.M*, Sydney, 622, 1998.

Mallard, "The noes have it! Do they?" *British J. Radiol.*, 54:831-849, 1981.

Mitchell, "Focal manifestations of diffuse liver disease at MR imaging," *Radiology*, 185:1-11, 1992.

Mitchell et al., "Liver and pancreas: improved spin-echo T1 contrast by shorter echo time and fat suppression at 1.5 $T^1$," *Radiology*, 178:67-71, 1991.

Mukundan, Jr. et al., "MR imaging of silicone gel-filled breast implants in vivo with a method that visualizes silicone selectivity," *J. Magn. Reson. Imaging*, 3(5):713-717, 1993.

Murakami et al., "Intensity correction of phased-array surface coil images," *Magn. Reson. Imaging*, 35:585-590, 1996.

Noll et al., "Homodyne detection on magnetic resonance imaging," *IEEE Trans. Med. Imaging*, 10:154-163, 1991.

Pfleiderer et al., "In vivo $^1H$ chemical shift imaging of silicone implants," *Magn. Reson. Med.*, 29(5):656-659, 1993.

Proctor and Yu, "The dependence of a nuclear magnetic resonance frequency upon chemical compound," *Phys. Rev.*, 77:717, 1950.

Pruessmann et al., "Spiral SENSE: sensitivity encoding with arbitrary K-space trajectories," *Proc. ISMRM 7th Ann. Mtg.*, Philadelphia, 94, 1999.

Pruessmann et al., "SENSE: sensitivity encoding for fast MRI," *Magn. Reson. Med.*, 42:952-962, 1999.

Pruessmann et al., "Coil sensitivity encoding for fast MRI," *Proc. ISMR.M 6th Ann. Mtg.*, Sydney, 579, 1998.

Pruessmann et al., "Coil sensitivity maps for sensitivity encoding and intensity correction," *Proc. ISMRM 6th Ann. Mtg.*, Sydney, 2087, 1998.

Pykett and Rosen, "Nuclear magnetic resonance: in vivo proton chemical shift imaging," *Radiology*, 149:197-201, 1983.

Ra and Rim, "Fast imaging method using multiple receiver coils with subencoding data set," *Proc. SMRM 10th Ann. Mtg.*, San Francisco, 1240, 1991.

Ra and Rim, "Fast imaging using subencoding data sets from multiple detectors," *Magn. Reson. Med.*, 30: 142-145, 1993.

Riek et al., "Flow compensation in MRI using a phase-corrected real reconstruction," *Magn. Reson. Med.*, 30:724-731, 1993.

Roemer et al., "The NMR phased array," *Magn. Reson. Med.*, 16:192-225, 1990.

Rosen et al., "Hematologic bone marrow disorders: quantitative chemical shift MR imaging," *Radiology*, 169:799-804, 1988.

Runge et al., "Magnetic resonance imaging of multiple sclerosis: a study of pulse-technique efficacy," *Am. J. Roentgenol*, 143:1015-1026, 1984.

Rybicki et al., "Fast three-point Dixon MR imaging of the retrobulbar space with low-resolution images for phase correction: comparison with fast spin-echo inversion recovery imaging," *Am. J. Neuroradiol*, (22) 1798-1802, 2001.

Schneider and Chan, "Selective MR imaging of silicone with the three-point Dixon technique," *Radiology*, 187(1):89-93, 1993.

Sepponen et al., "A method for chemical shift imaging: demonstration of bone marrow invovement with proton chemical shift imaging," *J. Comput Assist. Tomogr.*, 8(4):585-587, 1984.

Sibson et al., "In vivo evidence for a cerebral glutamate-glutamine cycle: $^{13}C$ NMR measurement of glutamine synthesis during high-dose pentobarbital anaesthesia," 5th ISMRM, 1456, 1997.

Skinner and Glover, "An extended two-point Dixon algorithm for calculating separate water, fat, and $B_0$ images" *Magn. Reson. Med.*, 37:628-630, 1997.

Sodickson and Manning., "Simultaneous acquisition of spatial harmonics (SMASH): fast imaging with radiofrequency coil arrays," *Magn. Reson. Med.*, 38:591-603, 1997.

Szumowski et al., "Phase unwrapping in the three-point Dixon method for fat suppression MR imaging," *Radiology*, 192:555-561, 1994.

Szumowski et al., "Double-echo three-point-Dixon method for fat suppression MRI," *Magn. Reson. Med.*, 34:120-124, 1995.

Tien, "Fat-suppression MR imaging in neuroradiology: techniques and clinical application," *Am. J. Roentgenol*, 158:369-379, 1992.

Twieg et al., "A general treatment of NMR imaging with chemical shifts and motion," *Magn. Reson. Med.*, 5:32-46, 1987.

Wehrli et al., "Mechanisms of contrast in NMR imaging," *J. Comput. Assist. Tomogr.*, 8(3):369-380, 1984.

Weiger et al., "Accelerated cardiac breathhold imaging using coil sensitivity encoding," *Proc. ISMRM 6th Ann. Mtg.*, Sydney, 799, 1998.

Weiger et al., "Cardiac real-time acquisition using coil sensitivity encoding," *Proc. ISMRM 6th Ann. Mtg.*, Sydney, 803, 1998.

Williams, "True water and fat MR imaging with use of multiple-echo acquisition," *Radiology*, 173:249-253, 1989.

Xiang and Henkleman, "Motion artifact reduction with three-point ghost phase cancellation," *J. Magn. Reson. Imaging*, 1:633-642, 1991.

Xiang and An, "General 3-point water-fat imaging with optimized SNR," *Proc. 4th Ann. Scientific Mtg. Intl. Soc. Magnetic Resonance in Medicine*, NY Intl. Soc. Magn. Resonance in Medicine, 1544, 1996.

Xiang and Henkelman, "K-space description for MR imaging of dynamic objects," *Magn. Reson. Med.*, 29:422-428, 1993.

Xiang et al., "Two-point interference method for suppression of ghost artifacts due to motion," *J. Magn. Reson. Imaging*, 3:900-906, 1993

Xiang and An, "Water-fat imaging with direct phase encoding," *J. Magn. Reson. Imaging*, 7:1002-1015, 1997.

Yeung et al., "Single-acquisition chemical-shift imaging of a binary system with use of stimulated echoes," *Radiology*, 167:537-540, 1988.

Yeung and Kormos, "Separation of true fat and water images by correcting magnetic field inhomogeneity in situ," *Radiology*, 159:783-786, 1986.

Young et al., "Apparent changes of appearance of inversion-recovery images," *Mag. Res. Med.*, 2:81-85, 1985.

Zhu et al., "A robust water and fat separation method," *Proc. 4th Ann. Scientific Mtg. Soc. Magn. Resonance*, NY Soc. Magnetic Resonance, 1542, 1996.

* cited by examiner

METHODS AND APPARATUSES FOR FAST CHEMICAL SHIFT MAGNETIC RESONANCE IMAGING

REFERENCE TO RELATED APPLICATIONS

This is a divisional patent application which claims priority to and the benefit of U.S. application Ser. No. 10/882,111, filed Jun. 30, 2004, now U.S. Pat. No. 7,084,626 titled Methods and Apparatus for Fast Chemical Shift Magnetic Resonance Imaging, which is incorporated herein by reference in its entirety.

FIELD OF THE INVENTION

The invention relates generally to the field of medical imaging. More particularly, the invention relates to fast magnetic resonance imaging of different chemical species, such as in imaging of water, fat, and silicone implants.

DISCUSSION OF THE RELATED ART

Magnetic resonance imaging (MRI) can be used to generate chemical shift specific images because protons in different chemical species may have different resonance frequencies. For in vivo tissues, the two most dominant chemical species are water and fat, whose resonance frequencies are separated by approximately 3.5 ppm (parts per million), or 220 Hz at 1.5-Tesla field strength. Multi-point Dixon (MPD) can also be used to separate water and fat images by encoding the phase difference between water and fat signals into images with different echo shifts and by subsequent post-processing. One advantage of the MPD techniques is that field inhomogeneity effects on the images can be completely removed in post processing. However, the MPD technique requires the acquisition of multiple images, which leads to increased total scan time.

An estimated 2 million women in the United States alone have silicone breast implants. Because ruptures or leakages may pose significant health risks, accurate radiological evaluation of the additional chemical species, such as silicone breast implants is of high importance. Presently, the most widely used diagnostic modalities for silicone breast implant evaluation are x-ray mammography and ultrasound sonography. Unfortunately, the radiological findings using these techniques are generally not conclusive.

Magnetic resonance imaging (MRI) has proven useful in the diagnosis of ruptures or leakage of silicone gel-filled implants and, in general, is more sensitive than competing modalities. One of the primary reasons for this high sensitivity is due to the fact that MR imaging facilitates the acquisition of silicone-specific images in the breast, permitting unequivocal determination of intra- or extracapsular ruptures of silicone-based prostheses.

There are generally two types of methods for generating silicone-specific images using MR. The first is the frequency selective method. One possible implementation is to use a frequency-selective excitation or refocusing pulse centered on the resonance frequency of silicone in conjunction with other techniques to suppress the water and lipid signals. Since resonance frequency of fat and silicone are too close to separate robustly based on resonance frequency, fat suppression is often achieved via the use of short-tau inversion recovery pulse sequence, which takes advantage of the characteristically short longitudinal relaxation time of fat.

Another potential implementation is to use a combination of two preparatory pulse sequences before the acquisition of silicone images. The first sequence is the short-tau inversion recovery (STIR), which is used to suppress the fat signals based on its short longitudinal relaxation time. The second sequence is the chemical saturation (ChemSat) sequence, which is used to suppress the water signals based on its chemical shift. While these techniques may provide clinically useful images, the image quality that is achieved could be sub-optimal or inconsistent under different scan configurations because of the techniques' intrinsic sensitivity to the magnetic field inhomogeneity.

Another method that produces silicone-specific images is the phase-selective method. The Dixon technique, originally proposed to generate separate water and fat-only images, belongs to this category. In order to be adapted to the silicone implant imaging, previous investigators have assumed that the frequency separation between silicone and water resonance is a multiple of the silicone and fat resonance frequency difference. Such an assumption was necessary because of the presence of the three distinct chemical species (water, fat, and silicone) in contrast to the water/fat imaging where only two chemical species (water and fat) are involved. One obvious drawback of this approach is that the above assumption is not realistic.

Furthermore, even if the assumption is valid, the method can only be used with the traditional symmetric Dixon sampling where the two chemical species under consideration are set to be strictly either in-phase or 180 degrees out-of-phase. Using asymmetric sampling, which has been shown to offer increased time efficiency and processing reliability, would put water and fat out of phase, and therefore render the Dixon approach completely inapplicable to silicone imaging. Consequently, this approach is limited in time-efficiency and reliability. This method also requires relatively long acquisition times, often leading to reduced slice coverage, compromised imaging parameters or exacerbated motion artifacts.

Initial comparisons between the frequency and phase selective methods in the literature demonstrate the degradation of diagnostic quality associated with the limitations of the phase-selective approach. Recently, more sophisticated approaches relying on spectral modeling have been introduced. While these models make no assumptions about the frequency spectrum, they do require extensive post-processing involving inversion of potentially unstable matrices. As for the Dixon technique, the spectral modeling technique also requires long acquisition time, and scan parameters that can be used are therefore limited due to patient comfort and motion.

SUMMARY OF THE INVENTION

There is a need for the following embodiments. Of course, the invention is not limited to these embodiments.

According to an aspect of the invention, a method comprises: obtaining a plurality of MRI data signals using a Dixon technique combined with an inversion recovery technique, such as a short tau inversion recovery (STIR) technique, and processing the plurality of MRI data signals using a Dixon reconstruction technique to create a chemical shift image.

According to another aspect of the invention, a method comprises: obtaining a plurality of magnetic resonance imaging data signals using a Dixon technique combined with a encoding reconstruction technique (SENSE), and processing the plurality of magnetic resonance imaging data signals using a sensitivity and a Dixon reconstruction technique to create a chemical shift image.

According to yet another aspect of the invention, an apparatus comprises: a MRI scanner for obtaining images, a controller configured to provide input to the scanner to acquire images using a Dixon technique combined with a short tau inversion recovery (STIR) technique to produce a plurality of MRI data signals, and processing the plurality of MRI data signals using a Dixon reconstruction technique to create a chemical shift image, and an output device to display the resulting image.

These, and other, aspects of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions, and/or rearrangements may be made within the scope of the invention without departing from the spirit thereof, and the invention includes all such substitutions, modifications, additions, and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

FIG. 7A is the water-only image, and FIG. 7B is the silicon-only image.

FIG. 8B is the water-only image, and FIG. 8C is the fat-only image.

DETAILED DESCRIPTION

Figure 1:
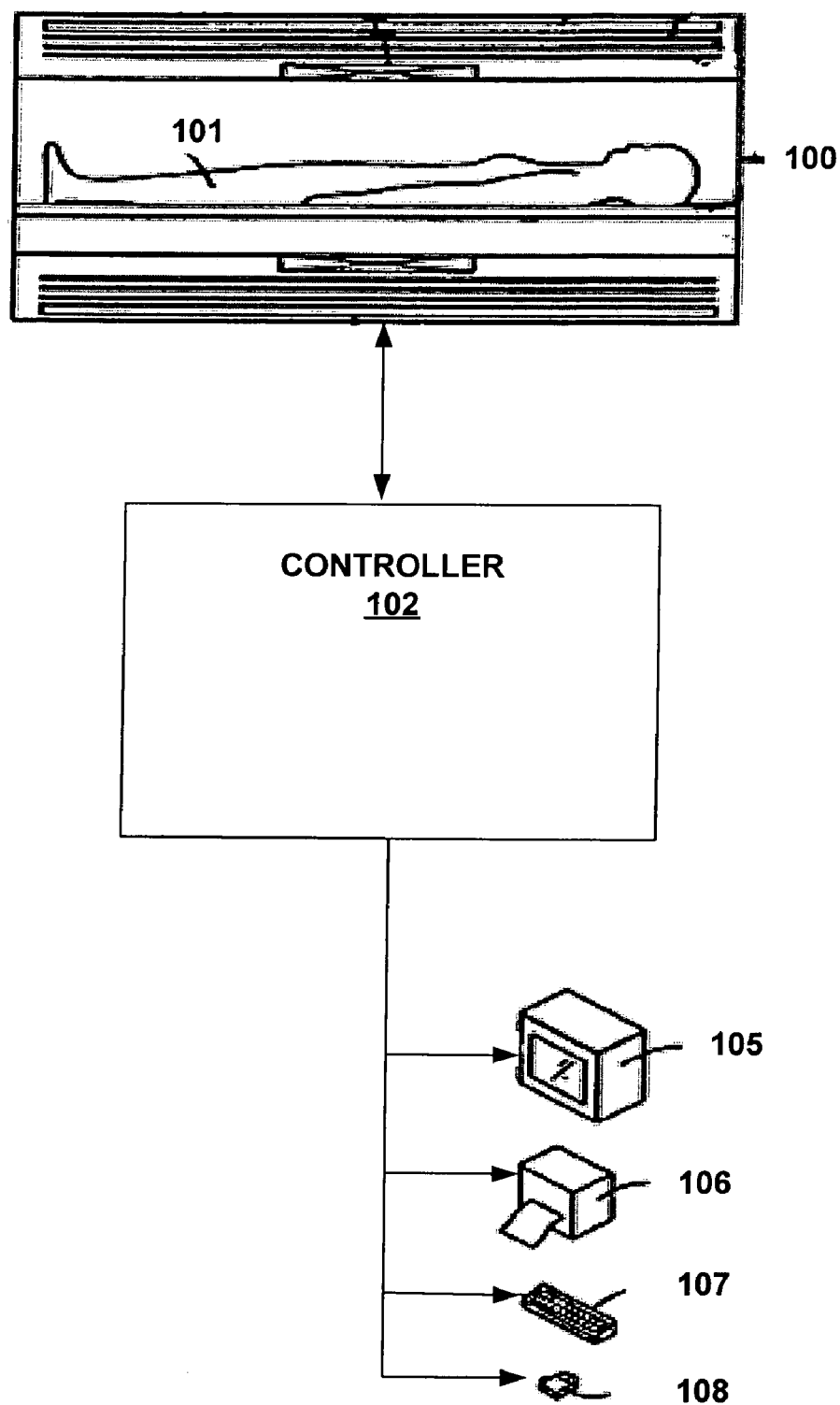
FIG. 1 illustrates an MRI imaging system in accordance with an embodiment of the present invention.

The invention and the various features and advantageous details thereof are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

MRI (magnetic resonance imaging) has been shown to be able to generate unique chemical shift images. In one embodiment of the invention, MRI may be used to generate unique silicone-specific and water-specific images and has been shown to be a sensitive and specific technique, particularly, in equivocal cases of extracapsular ruptures. MRI may be used to acquire silicone-specific images in anatomic locations such as in the breast, permitting unequivocal determination of extracapsular ruptures of silicone-based prostheses.

According to an embodiment of the invention, by combining an inversion recovery technique and the Dixon technique, no assumption about the frequency relationship between any three distinct chemical species present (water, fat, silicone, blood, cerebral fluids, etc.) is necessary; only the frequency relationship between the two remaining chemical species need to be considered. This allows the Dixon technique to robustly process the remaining two chemical species. In addition, more flexible and more reliable asymmetric sampling scheme and a spin echo (e.g., a fast spin echo) Dixon implementation may be used, making the invention as efficient as conventional imaging.

The present invention includes a method and apparatus for chemical shift imaging using a Dixon acquisition technique in combination with a short-tau inversion recovery techinique (STIR). According to embodiments of the invention, a method is provided for silicon-specific imaging using a fast Dixon technique for separation of silicone and water with inversion recovery fat suppression. A breast with implanted silicone prosthesis was imaged in a volunteer. Excellent fat suppression and separation between silicone and water were demonstrated across the field of view using acquisition parameters comparable to existing clinical techniques. The present invention is capable of overcomes several intrinsic limitations of the previously published techniques and may be used for robust and more efficient chemical shift imaging. In one embodiment, the technique may be use for silicone-specific imaging.

An image reconstruction algorithm may be used in this implementation to tailor the processing of the Dixon data to deal with the water and silicone specific images, instead of water and fat, as in the original Dixon implementation. This implementation may be implemented as a software option on an MR (magnetic resonance) scanner and used for imaging of different chemical species and is not limited to the imaging of silicone breast implants.

In accordance with an embodiment of the present invention, a fast spin-echo based inversion recovery pulse sequence was modified to incorporate a Dixon data acquisition, which may be a 2-point Dixon, or a fast 3-point Dixon (fast Dixon) data acquisition or other Multi-point Dixon (MPD) acquisition techniques. The fast 3-point Dixon data acquisition technique is disclosed in pending U.S. patent application Ser. No. 10/255,210, filed on Sep. 26, 2002, the entirety of which is incorporated herein by reference. As in a previously published frequency-selective technique, robust fat suppression is achieved before excitation using an adiabatic inversion pulse and by selecting an inversion time (TI) optimized for nulling the fat signal at a specific magnetic field strength. Separation between water and silicone is achieved through Dixon acquisition and processing.

In one embodiment of the invention, in order to increase the time efficiency, a fast 3-point Dixon implementation was used for data acquisition. In comparison to previous Dixon implementations in which readout gradients are shifted in position, this implementation affects echo shifts by inserting a pair of gradient lobes with opposite polarity before and after the readout gradient. Consequently, no increase in echo spacing is necessary and spatial coverage of significantly more slices can be achieved for given scan time and scan parameters.

By combining the inversion recovery for fat suppression with the fast spin echo based, fast Dixon technique for water and silicone separation, high-quality silicone-specific images may be obtained efficiently with imaging parameters comparable to conventional techniques. In comparison to the previously known techniques, no assumption about the inter-relationship among the water, fat, and silicone resonances is made. The magnetic field inhomogeneity effect, which often renders the frequency-selective techniques sub-optimal, may be compensated.

The method disclosed here is based on a phase selective approach. Dixon techniques, such as MPD were originally developed for separation of two dominant chemical species that are present in human body, namely fat and water. The general scheme behind Dixon techniques is to acquire multiple images, varying the relative phase shifts for the different chemical species in question between the images. Subsequent image processing may be used to re-combine the images arithmetically and generate unique images for each chemical species. An appealing advantage of the Dixon techniques is that effects of field inhomogeneities may be compensated for during the image reconstruction process, removing a major source of failure for the frequency-selective based techniques. A disadvantage of the technique is that multiple acquisitions are required, leading to longer scan times.

With the present invention, both fat suppression and separation between water and silicone become insensitive to field inhomogeneity. The problem of long scan time associated with Dixon acquisitions is mitigated via use of a modified fast spin-echo sequence for acquisition of the Dixon images, and when necessary further reduced by combining the fast Dixon technique with the partially parallel imaging technique such as SENSE. The latter technique is widely being used in the field of MRI as a fast imaging technique via undersampling of the image data and subsequent de-aliasing of the wrapped images using the receiver coil sensitivity profiles. Conventional application of the SENSE technique, however, generates only magnitude images. Combination of the MPD and SENSE techniques, in contrast, requires complex (both magnitude and phase) SENSE images and the result, as in the conventional SENSE implementation, is an acquisition time reduction by several factors for the MPD technique. Alternatively, the combination of any of the SENSE implementations with any of the MPD implementations without STIR may be used to improve the efficiency of Dixon techniques in separating water and fat in the absence of the silicone.

In FIG. 1, an MRI apparatus, in accordance with an embodiment of the present invention, is presented. The MRI apparatus includes a scanner 100, a controller 102, output devices such as a display screen 105, an output printing device 106, and input devices such as a keyboard 107 and a mouse 108.

Figures 2, 3:
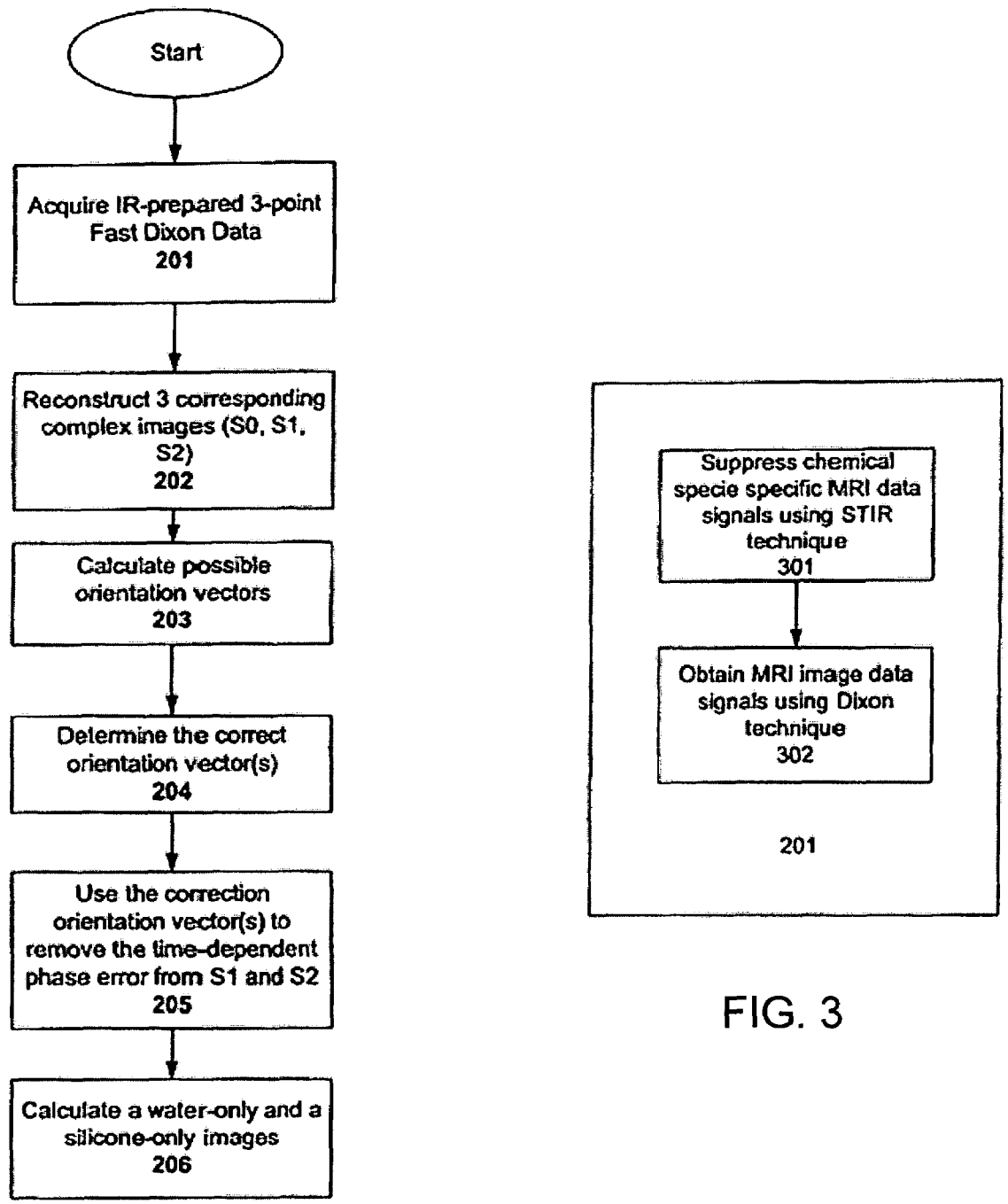
FIG. 2 is a flowchart showing steps of a method in accordance with an embodiment of the present invention.
FIG. 3 is a flowchart showing steps of a method in accordance with an embodiment of the present invention.

To obtain an image, a patient 101 is placed inside a scanner 100, which receives instructions about generating image data from the controller 102. The controller 102 obtains the data, processes the data to obtain desired image(s), and outputs the final image(s) to an output device of choice, such as a display monitor 105 or a printer 106. One of the various methods that may be utilized by the controller 102 is shown in FIG. 2. The controller 102 may also receive user input from input devices such as a keyboard 107 or a mouse 108 which dictates the type of images that are taken of the patient 101.

A flowchart showing the steps of an embodiment of the present invention is given in FIG. 2. In step 201, MRI image data is obtained from a subject using a three-point Dixon technique. Alternatively, other implementation of the MPD technique such as a two-point Dixon technique may be used. Steps 202-206 comprise a Dixon reconstruction scheme. Three complex images (S0, S1, S2) are created from the processed data in step 202. Steps for correcting phase error of the images take place in steps 203 through 205. In step 203, the time-independent phase information is removed from the three images and two possible orientation vectors are calculated using direct phase encoding. The correct orientation vectors are determined in step 204 and used to remove time-dependent phase error from images S1 and S2 in step 205. In step 206, these images may be used to calculate a water-only and a silicon-only image.

In step 202, three complex images are acquired with different time shifts $\Delta t = \tau_0$, $\tau_0+\tau$, and $\tau_0+2\tau$, corresponding to a sampling scheme of $(\alpha_0, \alpha_0+\alpha, \alpha_0+2\alpha)$, which can be expressed as $$S_0 = (W+CF)P_0 \qquad \text{Eq. 1}$$

$$S_1 = (W+CAF)P_0 P_1 \qquad \text{Eq. 2}$$

$$S_2 = (W+CA^2F)P_0 P_1^2 \qquad \text{Eq. 3}$$

where W and F are real and non-negative variables representing magnitudes of the magnetization vectors of 2 chemical species being imaged such as water and fat or water and silicone, C and A are know complex phase factors or phasors due to chemical shift, defined as $$C = \exp(i\Delta\omega\tau_0) = \exp(i\alpha_0) \qquad \text{Eq. 4}$$

$$A = \exp(i\Delta\omega\tau) = \exp(i\alpha) \qquad \text{Eq. 5}$$

where $\Delta\omega$ is the difference in Larmor frequency between 2 species, $\alpha$ is a phase angle, and $P_0$ and $P_1$ are unknown phasors representing phase errors, which can be written as $$P_0 = \exp(i\Phi)\exp(i\gamma\Delta B_0 \tau_0) \qquad \text{Eq. 6}$$

$$P_1 = \exp(i\gamma\Delta B_0 \tau) \qquad \text{Eq. 7}$$

For simplicity, two new complex variables X and Y are defined as $$X = W\, P_0\, P_1 \qquad \text{Eq. 8}$$

$$Y = C\, A\, F\, P_0\, P_1 \qquad \text{Eq. 9}$$

where W and F are the magnitudes of X and Y. From equations 1-3, $$S_1 = X + Y \quad \text{Eq. 10}$$

$$S_0 S_2 = X^2 + Y^2 + XY(A + 1/A) \quad \text{Eq. 11}$$

It is straightforward to obtain the following two sets of possible solutions for X and Y $$\begin{cases} X_1 = \dfrac{S_1 + \Delta I}{2} \\ Y_1 = \dfrac{S_1 - \Delta I}{2} \end{cases} \quad \text{Eq. 12}$$

or $$\begin{cases} X_2 = \dfrac{S_1 - \Delta I}{2} \\ Y_2 = \dfrac{S_1 + \Delta I}{2} \end{cases} \quad \text{Eq. 13}$$

where ΔS is defined as $$\Delta S = \dfrac{\sqrt{(A+1)^2 S_1^2 - 4A S_0 S_2}}{A - 1} \quad \text{Eq. 14}$$

There are two possible solutions of (X, Y), symmetrically related as $X_1 = Y_2$ and $Y_1 = X_2$, due to the square-root operation in Eq. 14. This ambiguity cannot be resolved from equations 10-11 where X and Y have symmetric positions. However, if the definition of X and Y in Eqs. 8-9 are used, the correction answer can be found as long as the condition $CA \ne \pm 1$ is fulfilled If CA is not 1 or −1, according to Eqs. 8-9, there is a definite phase relationship between the two vectors X and Y. Namely, the correct vector X either takes a leading or lagging position relative to Y, depending on the timing parameter Δt. Therefore, W and F should simply be the magnitudes of the X and Y pair, of which the vector Y may be a leading vector. This relative phase relationship allows an unambiguous determination of the chemical species components directly from the complex equations on a pixel by pixel basis.

In steps 203-205, orientation vectors as defined below, may be determined and used to remove time-dependent phase information. The product of phase factors $P_0 P_1$ is a unit vector field. According to Eqs. 2 and 8-9, an orientation vector <O> field parallel to $P_0 P_1$ can be defined as $$O = X + Y/(CA) \quad \text{Eq. 15}$$

where X and Y are the solutions provided by Eq. 12 and 13. This correct orientation vector field should also change its direction smoothly as defined by the field of inhomogeneity. In embodiments where the incorrect solutions from Eq. 12 or 13 is used, the orientation vector may show discontinuity in its direction. As such, image filtering operations may be designed to smooth the direction of the orientation vectors and therefore, may correct the possible mis-selection of the solutions from Eq. 12 or 13.

In one embodiment of the present invention, in order to adapt the Dixon technique for silicone-specific imaging, a preparatory pulse sequence with an inversion recovery technique, such as a short TI (inversion time) inversion recovery (STIR) may be used to suppress the fat signals before the Dixon data acquisition in step 201. As shown in FIG. 3, step 201 may comprise suppressing a plurality of chemical specie specific MRI data signals using a STIR technique 301, and obtaining MRI image data signals using a Dixon technique, such as fast Dixon 302.

Direct application of the Dixon technique to silicone specific imaging without fat suppression has to rely on the assumption that the frequency separation between silicone and water proton resonances is approximately a multiple of the silicone and fat resonance frequency difference. When this approximation is not valid, incomplete separation of silicone, water, and fat occurs since the technique essentially is designed for the separation of only two distinct chemical species. In one embodiment of the invention, this assumption is unnecessary because only two chemical species, water and silicone, are present after fat suppression, facilitating a direct application of the Dixon technique.

The long scan time required in acquiring the multiple images for the 3-point Dixon technique may be reduced using the fast Dixon technique. In principle, fast spin echo can be used to increase the scan efficiency over the conventional spin echo by a factor roughly equal to the echo train length selected. However, this ideal increase in scan efficiency was not achieved in earlier implementations of the fast spin echo based Dixon technique because the required echo shifts resulted in a corresponding increase in inter-echo spacing of the fast spin echo. Increased inter-echo spacing exacerbates image quality problems commonly associated with the use of the fast spin echo technique, such as ghosting and blurring due to T2 relaxation during readout which apodizes the signal in the phase-encoding direction. To minimize these effects, the fast Dixon technique, in which the required echo shifts are induced using a pair of bipolar gradients around the readout gradients as opposed to time-shifting the readout gradients themselves, was implemented. Using this technique, inter-echo spacing as well as the fast spin-echo efficiency is preserved for the Dixon acquisition and thereby minimizing the exacerbation of artifacts due to an increase in the echo spacing.

In order to further speed up the data acquisition, the Dixon technique may be combined with a partially parallel imaging technique, such as the sensitivity encoding (SENSE) technique. The SENSE technique is based on measuring receiver coil spatial sensitivity profiles and using the information to reduce the data acquisition time by a factor that can be as high as the number of the receiver coils employed. The sensitivity profile of the receiver coil may be acquired in a separate scan or using low resolution image acquired during the Dixon scan. While the feasibility of the SENSE and the related techniques have been demonstrated for conventional magnitude images, it may be demonstrated that the technique can also be used for phase-imaging technique, such as the Dixon technique. The processing of the so-acquired data would proceed by reconstructing SENSE images with signal phase preserved and then process the resulting images with the Dixon algorithm to generate chemical species-specific images, such as water-specific or silicone-specific images.

Figure 4:
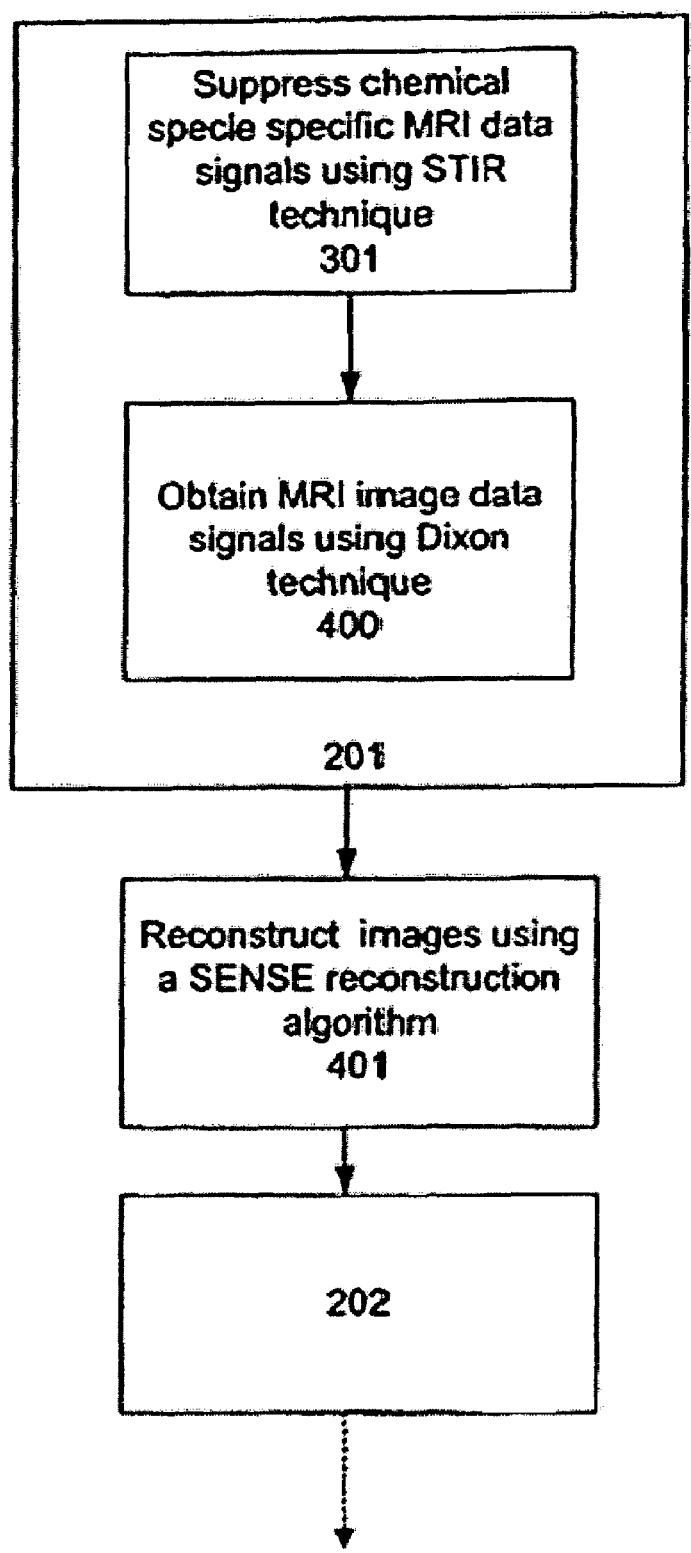
FIG. 4 is a flowchart showing steps of a method in accordance with an embodiment of the present invention.

As shown in FIG. 4, according to one embodiment of the invention, step 201 may comprise suppressing a plurality of chemical species specific MRI data signals using a STIR technique (step 301), and obtaining MRI image data signals using a Dixon technique, such as fast Dixon, that is modified to have a shorter acquisition time (step 400) than the method shown in FIG. 3. Following step 201 and before step 202, the method of the embodiment of the invention may comprise reconstructing images from the MRI image data signals using a SENSE reconstruction algorithm (step 401) before reconstructing the complex images of step 202 and the remainder of steps 203-206.

In some embodiments, a SENSE reconstruction algorithm (step 401), an imaging array of $n_c$ receiver coils may be used. Fourier encoding is described by a set of $n_k$ sampling positions in k-space. If the whole object is within the volume of interest (VOI), then a sample value m obtained from the γ-th coil at the κ-th position in k-space is given by $$m_{\gamma,\kappa} = \int c(r) e_{\gamma,\kappa}(r) dr \quad \text{Eq. 16}$$

where r denotes 3D position, $$e_{\gamma,\kappa}(r) = e^{jk_\kappa r} s_\gamma(r) \quad \text{Eq. 17}$$

is the net encoding function composed of harmonic modulation and the complex spatial sensitivity $s_\gamma$ of coil γ, and c results from tissue and sequence parameters. The effects of non-uniform k-space weighting due to relaxation may be neglected.

From the linearity of encoding it is clear that image reconstruction is preferably substantially linear as well. That is, each of $n_v$ image values is to be calculated as a linear combination of sample values:

$$v_\rho = \sum_{\gamma,\kappa} F_{\rho,(\gamma,\kappa)} m_{\gamma,\kappa}, \quad \text{Eq. 18}$$

where ρ counts the voxels to be resolved. The transform F is referred to as the reconstruction matrix. Its size is $n_v \times n_c n_k$. Assembling sample and image values in vectors, image reconstruction may be rewritten in matrix notation:

$$v = Fm \quad \text{Eq. 19}$$

With such linear mapping the propagation of noise from sample values into image values may be described by noise matrices. The ρ-th diagonal entry of the image noise matrix X represents the noise variance in the ρ-th image value while the off-diagonal entries reflect noise correlation between image values. As shown there, these matrices fulfil the relation $$X = F \tilde{\Psi} F^H \quad \text{Eq. 20}$$

The central objective in choosing a reconstruction matrix is to make each image value selectively reflect signal from the voxel it represents. To trace the origin of signal in image values, insert Eq. 16 into Eq. 18, to find $$v_\rho = \int_{VOI} c(r) \left( \sum_{\gamma,\kappa} F_{\rho,(\gamma,\kappa)} e_{\gamma,\kappa}(r) \right) dr. \quad \text{Eq. 21}$$

The term in brackets describes the spatial weighting of signal in $v_\rho$. It is therefore called the corresponding voxel function:

$$f_\rho(r) = \sum_{\gamma,\kappa} F_{\rho,(\gamma,\kappa)} e_{\gamma,\kappa}(r) \quad \text{Eq. 22}$$

Hence, the matrix F is preferably chosen such that the resulting voxel functions approximate the desired voxel shapes. Let iρ(r) denote an orthonormal set of ideal voxel shapes, e.g., box functions. The relation between ideal voxel shapes and encoding functions is described by the $n_c n_k \times n_v$ encoding matrix $$E_{(\gamma,\kappa),\rho} = \int_{VOI} i^*_\rho(r) e_{\gamma,\kappa}(r) dr \quad \text{Eq. 23}$$

There are many possible ways of approximating ideal voxels. Two concepts are discussed here as non-limiting examples. The first approach is to choose those voxel functions that exhibit the least square deviation from the ideal. This criterion entirely determines reconstruction; the approach is therefore referred to as the strong one. It has been shown that it yields $$F = E^H C^{-1}, \quad \text{Eq. 24}$$

where C denotes the correlation matrix of the encoding functions. The image noise matrix of Eq. 8 is then given by $$X = E^H C^{-1} \tilde{\Psi} C^{-1} E \quad \text{Eq. 25}$$

The second approach uses a different concept of similarity between real voxel functions and ideal shapes. It requires that each voxel function fulfill the orthonormality relations of its ideal counterpart:

$$\int_{VOI} i^*_\rho(r) f_{\rho'}(r) dr = \delta_{\rho,\rho'} \quad \forall \rho, \rho' \quad \text{Eq. 26}$$

Using Eq. 22 and 23, Eq. 26 may be rewritten in matrix form:

$$FE = Id_{n_v}, \quad \text{Eq. 27}$$

where $Id_{n_v}$ denotes $n_v \times n_v$ identity. By this condition, the reconstruction matrix F is generally not yet entirely determined. It leaves $n_c n_k - n_v$ degrees of freedom per voxel, which may be utilized for signal-to-noise reduction (SNR) optimization. To that end each diagonal element of the image noise matrix X is minimized, yielding $$F = (E^H \tilde{\Psi}^{-1} E)^{-1} E^H \tilde{\Psi}^{-1} \quad \text{Eq. 28}$$

In this case the image noise matrix reads $$X = (E^H \tilde{\Psi}^{-1} E)^{-1} \quad \text{Eq. 29}$$

The reconstruction Eqs. 24 and 25 permit image reconstruction from data obtained with hybrid gradient and sensitivity encoding. Both are numerically challenging as they imply the inversion of large matrices. However, the two concepts also exhibit important differences. The second approach is more convenient in that it does not require the calculation of the matrix C and poses the smaller inversion problem when $n_{84} < n_c n_k$. Furthermore, it yields optimized SNR. On the other hand, the first approach is always applicable, whereas the second algorithm works only if the condition of equation 32 can be fulfilled. In particular, for weak reconstruction the rank of the matrix E must be equal to $n_v$, thus $n_v < n_c n_k$ must hold. Moreover, the second approach is less robust in terms of ensuring voxel quality.

The limitations of weak reconstruction may be understood by considering Dirac distributions as ideal voxel functions:

$$i_\rho(r) = \delta(r - r_\rho),\quad \text{Eq.30}$$

where $r_\rho$ denotes the center of the $\rho$-th voxel. The encoding matrix then reduces to $$E_{(\gamma,\kappa),\rho} = e_{\gamma,\kappa}(r_\rho) \quad \text{Eq.31}$$

In this case the weak criterion of Eq. 27 may be restated as follows: each voxel function must be equal to one in the center of the voxel it belongs to and equal to zero in all other voxels' centers. A voxel function with this property will be acceptable only as long as it is well behaved between voxel centers. In this view, the criterion becomes unreliable when there are solutions that vary considerably within voxels and at the same time yield favorably low noise.

Partially parallel imaging techniques such as SENSE have been developed to accelerate image acquisition by a factor up to the number of receiver coils used. In SENSE imaging, increased imaging speed is achieved by undersampling k-space along the phase-encoding direction, thus reducing the total number of phase encoding repetitions required for image acquisition. Individual receiver coil sensitivity profiles are used during image reconstruction to unwrap the resulting spatially aliased images. The SNR (signal-to-noise-ratio) of images acquired using the SENSE technique in regions of overlapped signals is reduced by a factor of at least the square root of the acceleration factor.

In an example to combine SENSE and MPD technique, water and fat were well-separated in a phantom experiment. While the SNR (defined as the signal amplitude for a region of interest (ROI) divided by its standard deviation) of the SENSE reconstructed image was found to be reduced by approximately a factor of $\sqrt{2}$ relative to the fully encoded image, the SNR of the MPD image had a corresponding gain of approximately 1.6.

The SENSE-type of techniques are rapidly developing into standard features on most MR scanners on the commercial market. By preserving the relative phase information between images in the SENSE reconstruction process, these results show that combining SENSE and MPD is feasible and advantageous. It can be used for separating two distinct chemical species in a system, such as but not limited to water and fat, or water and silicone.

A natural consequence of using Dixon acquisition with gradient induced echo shifts for the fast spin echo based MPD technique is that the signals are asymmetric for all acquired echoes with non-zero phase shifts between water and silicone. For phase correction, only the central symmetric portion of the data corresponding to the three echoes with shared k-space coordinates was used. Although images reconstructed from these data are generally of lower resolution than the final images, no significant negative impact is expected on the final image quality. The underlying reason is that phase errors due to field inhomogeneity and other system imperfections are, in general, spatially slow-varying. This fact may be exploited in phase correction techniques, such as partial Fourier reconstruction, in which low-resolution phase images are used regularly for increased robustness and image signal-to-noise ratio.

The Dixon phase correction algorithm used may include a region growing technique without direct phase unwrapping followed by subsequent low-pass filtering, similar to what is used for Dixon water and fat separation. Region growing starts with a randomly selected seed or seeds and proceeds by seeking directional smoothness of a predefined orientation vector field. As in the case for water and fat imaging, the orientation vector is defined from two sets of solutions to the signal equations. When the correct solution is chosen, the orientation vector of a given pixel is parallel to the direction of the local field inhomogeneity. With an incorrect choice, the orientation vector will be either 90° or −90° away from the direction of the local field inhomogeneity. Once a smooth orientation vector field is obtained by the region growing and low-pass filtering process, it may be used to correct phase errors in the images reconstructed using all the acquired data. After this, simple arithmetic manipulation analogous to the calculations performed in 3-point Dixon for separation of water and fat can be used to generate water-only and silicone-only images.

EXAMPLES

The following examples are included to demonstrate specific embodiments of this disclosure. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

In one implementation of an embodiment of the invention, before the acquisition of the Dixon data, the frequency separation between water and silicone in a phantom was measured to be 240 Hz, in comparison to 215 Hz for the separation between water and fat. These values were used to determine the areas of the bipolar gradients used for echo shifting in the fast spin echo sequence for both phantom and human imaging described below. Three echoes with relative phase shifts of 0°, 90°, and 180° between water and silicone were collected in an interleaved manner by adjusting the area of the bipolar gradients before and after the readout gradients.

For phantom imaging, a bottle of cooking vegetable oil (Federated Group, Inc., Arlington Heights, Ill.), a bottle of distilled water solution with copper sulfate pentahydrate and sodium chloride, and a silicone breast implant (Mentor, Santa Barbara, Calif.) were imaged using the pulse sequence and reconstruction algorithm. The same pulse sequence and reconstruction algorithm were also used to image the breast of a patient with a bi-compartmental implant of silicone and saline. The phantom and human imaging was performed using a head and bilateral phased-array breast coil (MR Devices, Waukesha, Wis.), respectively. Imaging parameters used were TR/TE/TI: 3350/68/150 ms, echo train length (ETL)=12, FOV=18 cm, slice thickness/gap=4 mm/1 mm, acquisition matrix=256×192 and receiver bandwidth=16 kHz. A single acquisition of 20 slices took 5:35 minutes of scan time.

Figure 5B:
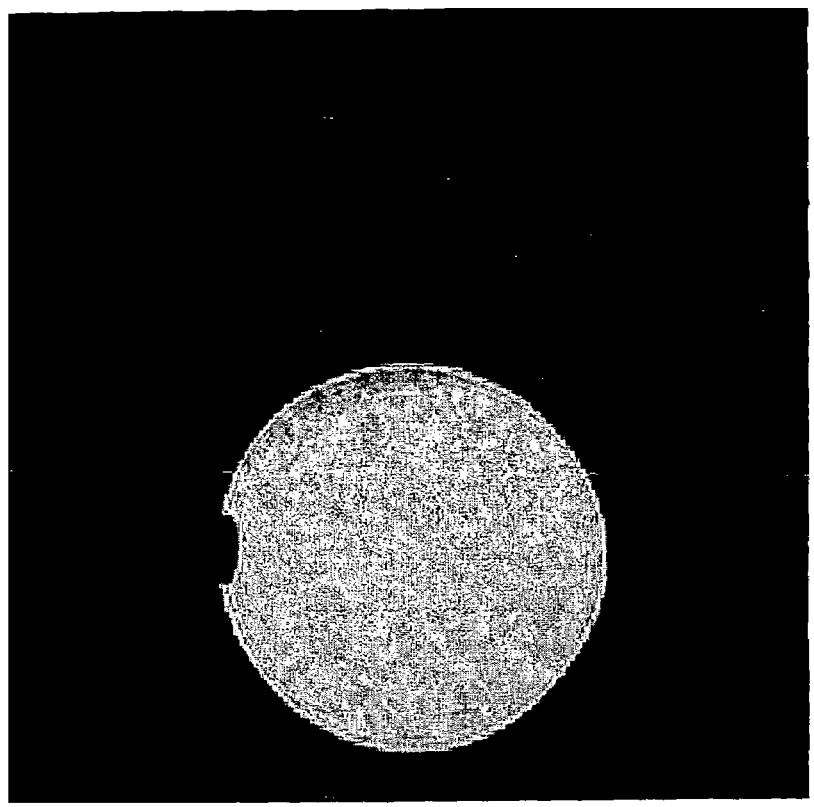
FIGS. 5A-5C are phantom images illustrating pre-processing and post-processing by a method in accordance with an embodiment of the present invention.
Figure 5A:
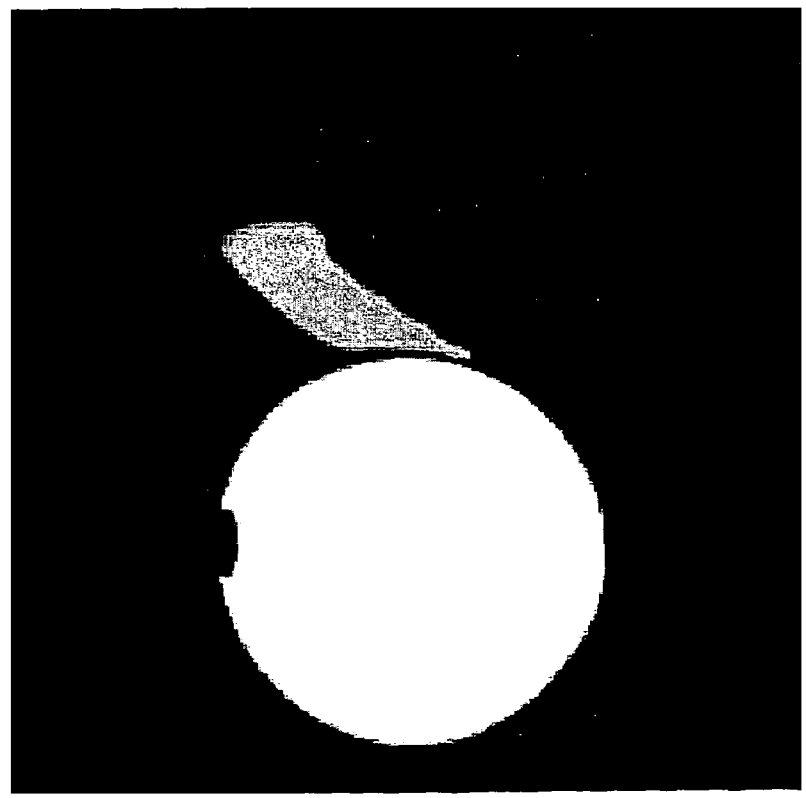
Figure 5C:
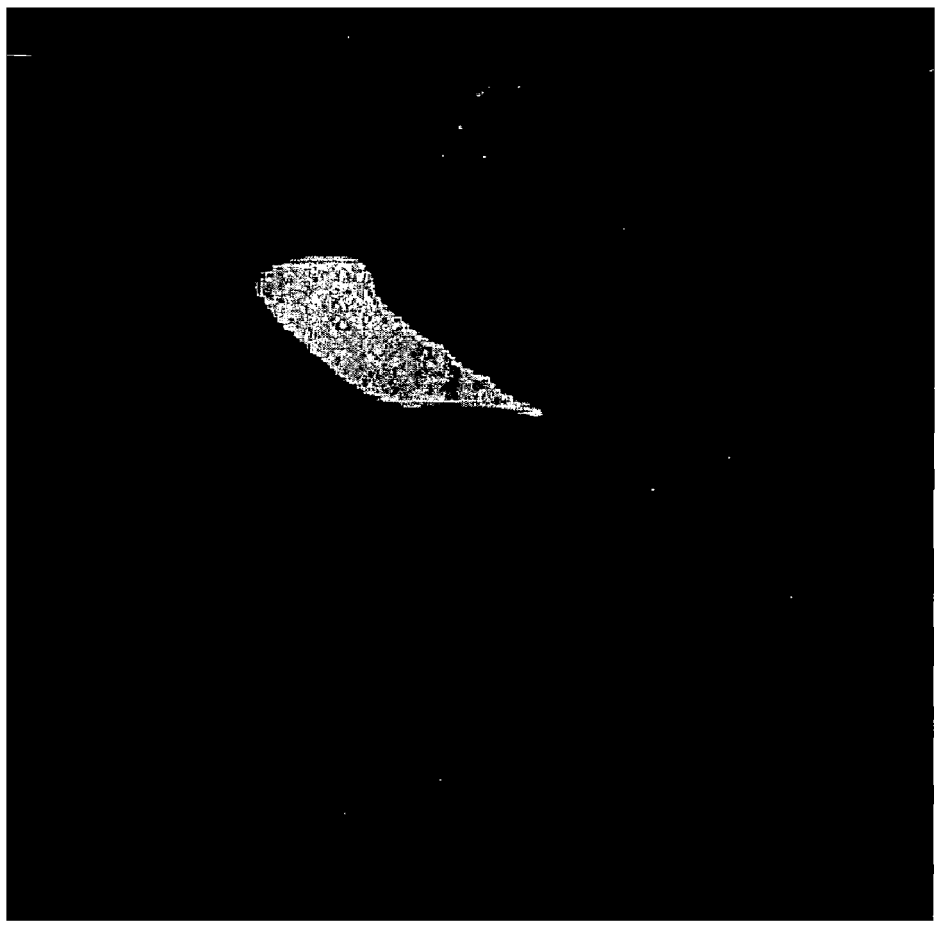

Application of the technique in phantom produced high quality water-only and silicone-only images. FIGS. 5A-5C show the phantom image prior to Dixon processing, the processed water-only and the processed silicone-only images, respectively. These images demonstrate that STIR suppresses fat signals while the MPD technique separates the remaining water and silicone signals. As mentioned previously, use of frequency-selective methods, such as the chemical shift selective technique, to obtain a silicone-only image would be more dependent on the achievable magnetic field homogeneity.

Figure 6B:
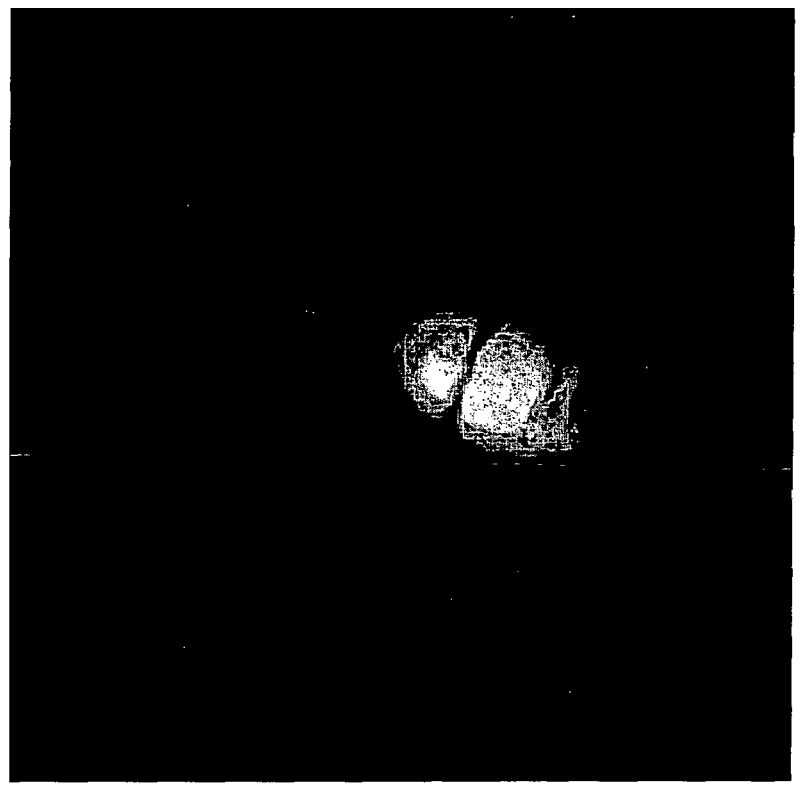
FIG. 6B is a silicon-only image of a breast cancer patient at a location of an implant created in accordance with an embodiment of the present invention.
Figure 6A:
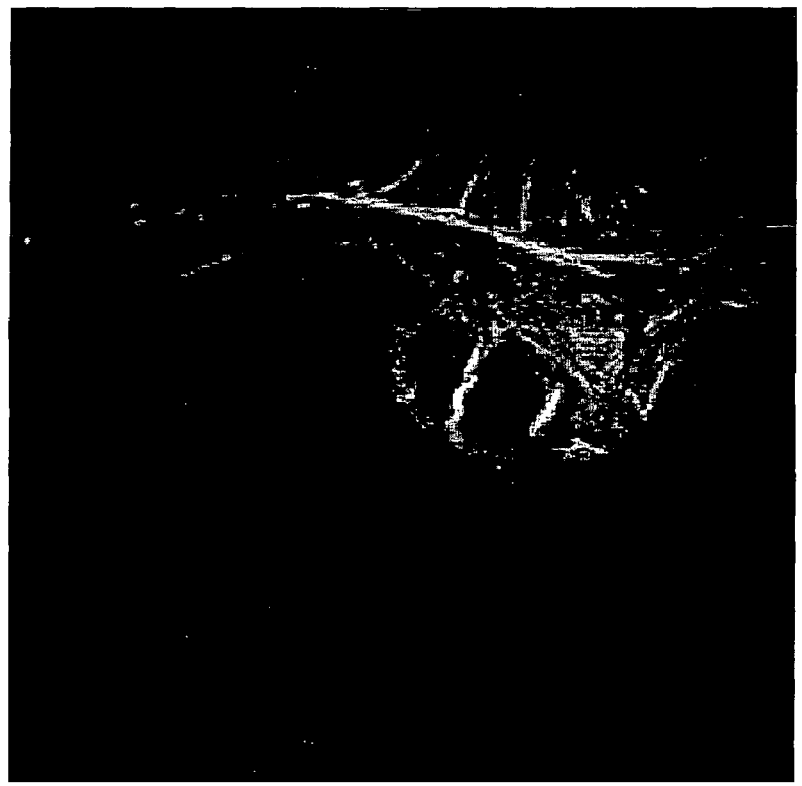
FIG. 6A is a water-only image of a breast cancer patient at a location of an implant created in accordance with an embodiment of the present invention.
Figure 7B:
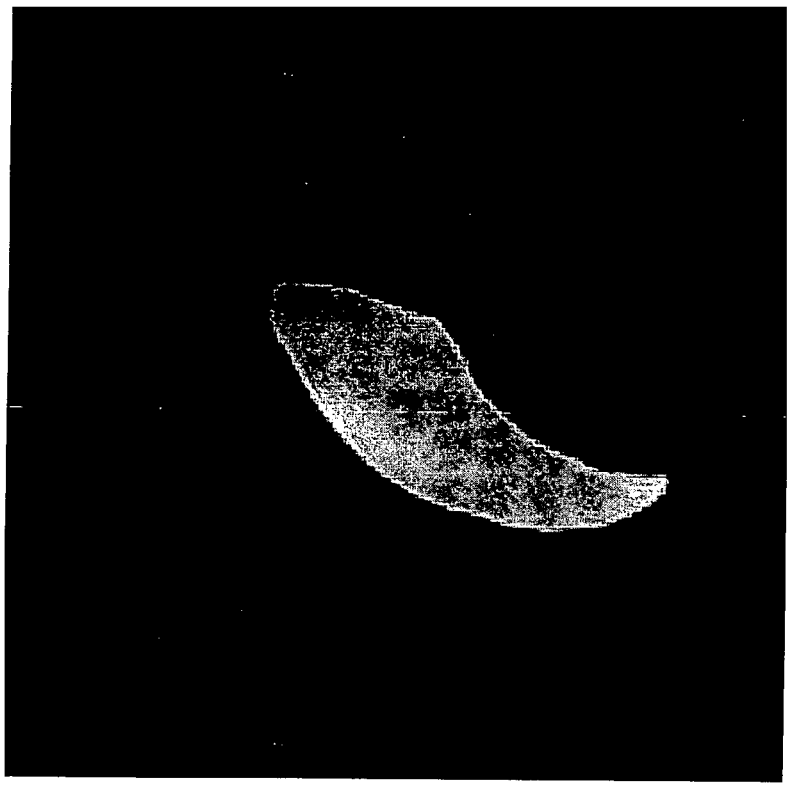
FIGS. 7A-7B are water-only and silicon-only breast images of a breast cancer patient produced in accordance with an embodiment of the present invention.
Figure 7A:
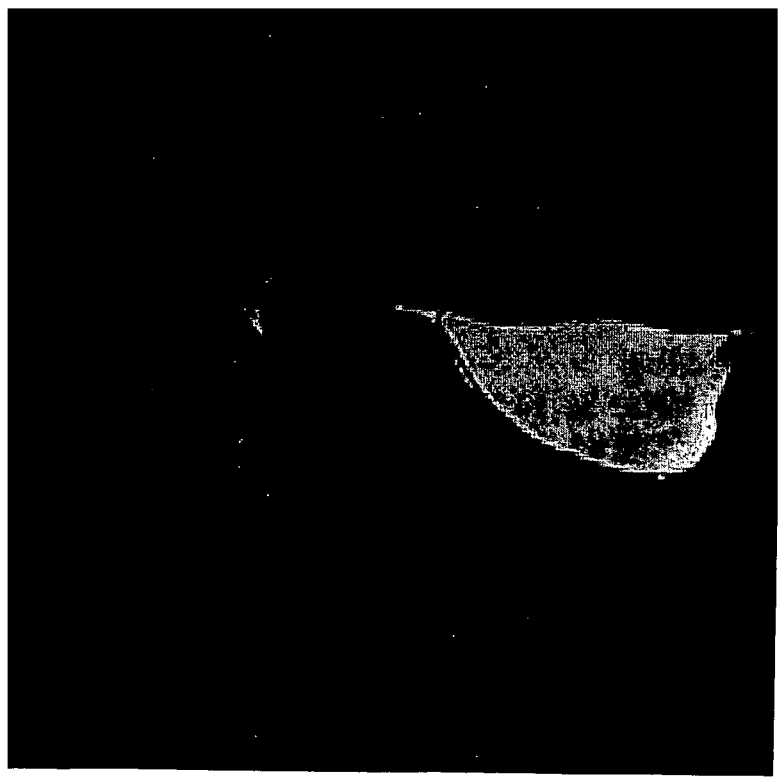

Imaging of a silicone implant in vivo demonstrated the ability of the sequence to provide clinically useful water-only and silicone-only images. FIG. 6A shows the water-only image and FIG. 6B shows the silicone-only images of a breast cancer patient at a location of the implant with only silicone component. FIGS. 7A-7B show water-only and silicone-only breast images of a breast cancer patient produced in accordance with embodiments of the present invention. FIG. 7A is the water-only image and FIG. 7B is the silicone-only image. The effectiveness of the technique in suppressing fat and separating water and silicone in vivo is again demonstrated. Interestingly, the saline component of the implant is visualized in the water-only image because of its identical resonance frequency with biological water.

Figure 8B:
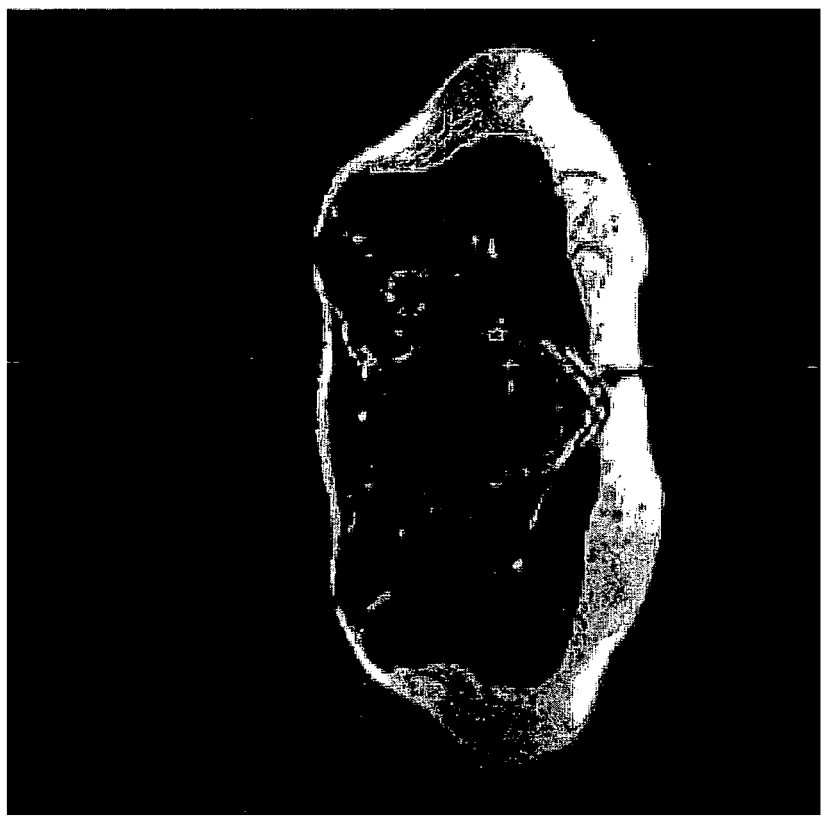
FIGS. 8B-8C are water-only and fat-only images of a pelvis produced in accordance with an embodiment of the present invention.
Figure 8A:
FIG. 8A is an image of a pelvis acquired in accordance with an embodiment of the present invention.
Figure 8C:
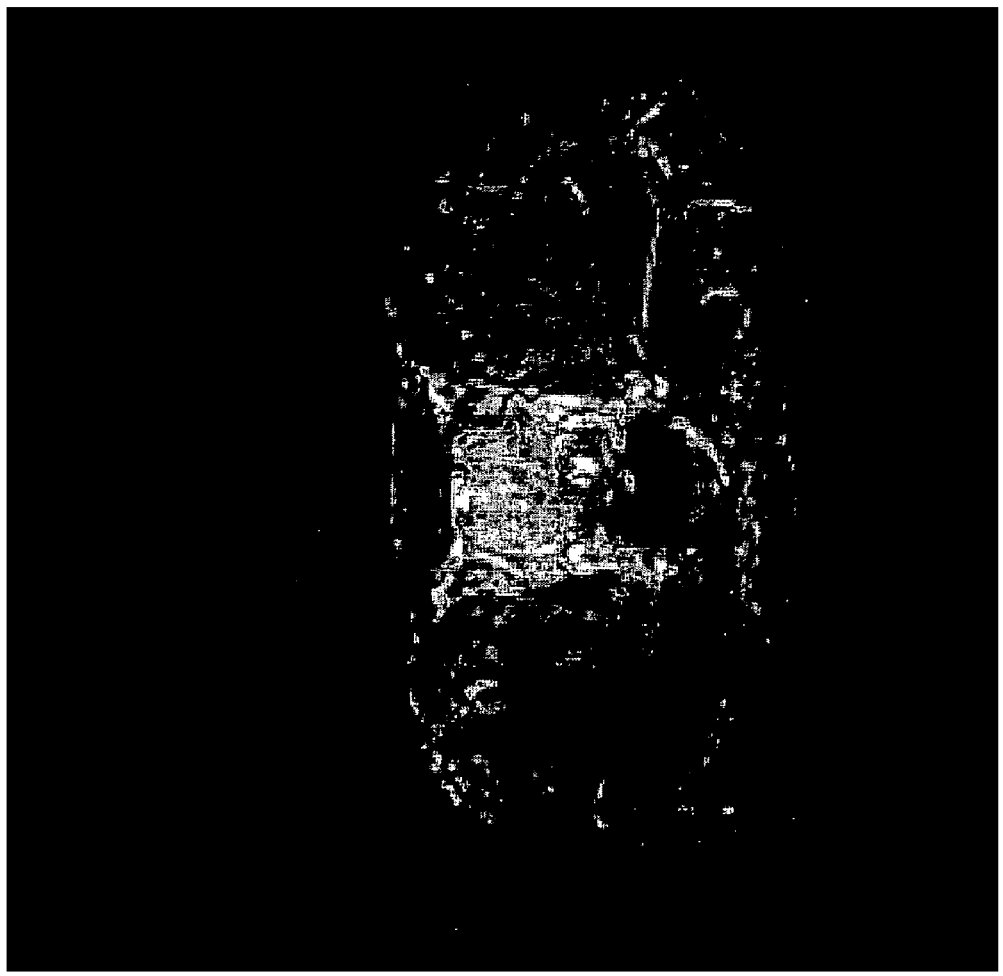

For an in vivo demonstration, FIG. 8A shows the T2-weighted image of a volunteer with aliasing after direct fast Fourier transform (FFT) reconstruction. The processed water-only and fat-only images (FIG. 8B and FIG. 8C, respectively) illustrate the full field of view (FOV). SENSE-MPD reconstruction and uniform spectral separation of water and fat achieved over the entire FOV. The feasibility of a combined SENSE-MPD technique both in phantom and in vivo has thus been demonstrated and the two techniques have been found to be compatible and complementary. The combined technique results in a significant reduction in the acquisition time typically required for the MPD technique while achieving an SNR comparable to current chemical saturation techniques with similar protocols. The combination with SENSE can therefore increase the attractiveness of the Dixon technique for routine clinical use, especially when acquisition time is a limiting factor. Another benefit to combining SENSE and the Dixon technique is the increased spatial resolution of the images.

Among all the imaging modalities, MRI has the unique capability in producing silicone-specific images for the evaluation of the silicone implant integrity. Previous MRI methods used are either completely or partially dependent on frequency-selective techniques. Performance is therefore dependent on field homogeneity, leading to potential performance inconsistencies on a patient or scanner basis. By combining inversion recovery for fat suppression with the fast three-point Dixon technique for water and silicone separation and/or SENSE parallel imaging techniques, high-quality silicone-specific images can be obtained using imaging parameters comparable to conventional breast imaging techniques. This reduces the potential introduction of additional artifacts, such as motion, that have plagued previous attempts to use a Dixon technique for water and silicone separation and makes routine clinical use of the method much more feasible. The effects of magnetic field inhomogeneity, which can often render frequency selective techniques useless for diagnostic purposes, may be partially or wholly compensated for in the current technique.

The early implementation of the three-point Dixon technique for silicone specific imaging relied on an approximation regarding the inter-relationship between the resonance frequencies of the three chemical species. Even if this approximation were true, the direct application of the Dixon technique on a system with three chemical species would only work when the phase angle of the Dixon acquisition is set to the traditional values of 0° and 180°. Deviation from these values, for example, the 0°-90°-180° acquisition scheme used in the present invention, would put water and silicone out of phase, therefore break down the decomposition algorithm used for generating silicone-only images. This flexibility in choosing the phase offsets is critical for processing reliability of phase correction and for fast spin echo acquisition timing.

While the three-point Dixon acquisition still requires a total scan time three times that of a comparable scan with a single signal average, the final water-only or silicone-only images may have an equivalent SNR approximately equal to that of a regular scan with three signal averages. Since most breast MRI exams are done with multiple signal averages, the total scan time of the current Dixon implementation (5-6 minutes for an entire breast coverage) is not prohibitively long compared to current clinical practice and provides comparable image quality. As noted above, the acquisition time of the MPD techniques can be effectively reduced by combining a MPD technique with a partially parallel imaging technique. In one embodiment, a 2-point Dixon technique may be used.

Clinical study of the silicone implant patients also frequently requires imaging of the water component of the breasts. With the frequency-selective approach, this invariably involves a separate acquisition to generate silicone-suppressed or combined water and silicone images. With the multiple-point Dixon technique, both water-only and silicone-only images are generated from a single acquisition, making the Dixon technique actually more time efficient in these cases, assuming at least two signal averages are used to acquire each water-only and silicone-only image under the standard protocol, which is likely.

The present invention is capable of generating chemical shift images in a single acquisition and in the same or even less scan time with identical scan parameters used by current conventional techniques. No limiting assumptions about the inter-dependence of the resonance spectral distribution of the different chemical species are necessary. Furthermore, in one embodiment of the invention, the benefit of minimized field inhomogeneity dependence on the final images due to 3-point Dixon processing are realized. This technique is therefore believed to be a more robust, and possibly more sensitive, alternative to current techniques in the MR evaluation of silicone based breast implants. In cases where a single signal average provides acceptable SNR, it may be desirable to reduce the Dixon acquisition time and the potential associated motion artifacts by trading off SNR, such as through the combination of MPD and SENSE techniques.

REFERENCES

The following references are each incorporated herein by reference.

U.S. Pat. No. 6,208,139 B1
Ahn et al., *Magn. Reson. Imaging*, 4:110-111, 1986.
Ahn and Cho, *IEEE Trans. Med. Imaging*, 6:32-36, 1987.
Akkerman and Maas, In: *Proceedings of the 3rd annual scientific meeting of the Society of Magnetic Resonance*, Society of Magnetic Resonance, 649, 1995.
An and Xiang, In: *Quadrature 2-point water fat imaging*, Proc. 4th Annual Scientific Meeting of the Intl Soc. for MRI in medicine, NY, 1541, 1996.
An and Xiang, *Magn. Reson. Med.*, 46(1):126-130, 2001.
An and Xiang, In: *Chemical shift imaging with spectrum modeling*, Proc. 5th Ann. Sci. Mtg. Intl. Soc. Magnetic Resonance in Medicine, Vancouver, 1997.
Araki et al., *Radiology*, 150:95-98, 1984.
Axel, *J. Comput. Assist. Tomogr.*, 8:381-384, 1984.

Baierl et al., In: *Measurements of relaxation times in intracranial tumours-an approach to tissue discrimination*, MR 85 Meeting, Garmisch Partenkirchen, West Germany, 1985.

Bailes et al., *Clin. Radiol.*, 33:395-414, 1982.

Bankson et al., In: *Partially parallel imaging with phase-sensitive data: increased temporal resolution for MR thermometry*, Proc. Intl. Soc. Magnetic Resonance in Medicine, Hawaii, 2002.

Berkel et al., *N. Engl. J. Med.*, 326(25):1649-1653, 1992.

Bernstein et al., *Med. Phys.*, 16:813, 1989.

Bilbey et al., *Am. J. Roentgenol.*, 164:637-642, 1995.

Bottomley et al., *Med. Phys.*, 11:425-448, 1984.

Bradley and Newton, In: *Advanced imaging techniques*, Newton and Potts (Eds), Clavadel Press, San Anselmo, Calif., 15-61, 1983.

Brey and Narayana, *Med. Phys.*, 15:241-245, 1987.

Brown et al., *Proc. Natl. Acad. Sci. USA*, 79:3523-3526, 1982.

Bydder and Young, *J. Comput. Assit. Tomogr.*, (4):659-675, 1985.

Bydder et al., *J. Comput. Assist. Tomogr.*, 9:413-414, 1985.

Bydder et al., *J. Comput. Assist. Tomogr.*, 9:690-697, 1985.

Bydder et al., *Am. J. Roentgenol*, 139215-139236, 1982.

Carlsen and Jensen, In: *Reconstruction algorithm for images obtained with flexible multi-element synergy coils*, Proc. of the SMR 2nd Annual Meeting, San Francisco, 835, 1994.

Carr et al., *Am. J. Roentgenol*, 1432:15-24, 1985.

Coombs et al., *Society of Magnetic Resonance*, 647, 1995.

Dickinson, *Phys. Rev.*, 77:736, 1950.

Dixon, *Radiology*, 153:189-194, 1984.

Doyle et al., *Am. J. Roentgenol*, 138:193-200, 1982.

Droege et al., *Radiology*, 153:425-33, 1984.

Ehman et al., In: *Scientific program and book of abstracts*, Soc. Magn. Resonance in Medicine, $3^{rd}$ Ann. Mtg, NY/Berkeley, Calif.: Society of Magnetic Resonance in Medicine, 210, 1984.

Gadian et al., *J. Comput. Assist. Tomogr.*, 9:242-251, 1985.

Gao et al., In: *Effects on selective excitation and phase uniformity of orthogonal field gradient components.* Proc. $10^{th}$ Ann. Mtg. Soc. Mag. Resonance in Medicine, San Francisco: Society of Magnetic Resonance in Medicine, 132, 1991.

Gilderdale et al., *J. Comput. Assist. Tomogr.*, 9:835-838, 1985.

Glover et al., *Magn. Reson. Med.*, 18:371-383, 1991.

Glover, *J. Magn. Reson. Imaging*, 1(5):521-530, 1991.

Gorczyca et al., *Am. J. Roentgenol*, 1994. 162(2): p. 305-310, 1994.

Graham et al., *J. Magn. Reson. Imaging*, 5:695-701, 1995.

Griswold et al., In: *An RF array designed for cardiac SMASH imaging*, Proc. ISMRM 6th Annual Meeting, Sydney, 437, 1998.

Gyorffy-Wagner et al., In: *T1 and T2 measurements in cerebral tumours and normal brain tissue,.* European Soc. Nucl. Magn. Resonance, Switzerland, 1984.

Hajnal and Young, In: *Use of spatial phase distribution models to produce water and fat only imaging from single echo shifted data sets*, Proc. 3rd Ann. Sci. Mtg. Society of Magnetic Resonance, 650, 1995.

Hardy et al., *J. Magn. Reson. Imaging*, 5(2):181-185, 1995.

Harms et al., *J. Comput. Assist. Tomogr.*, 19(3):394-399, 1995.

Haselgrove and Prammer, *Magn. Reson. Imaging*, 4:469-472, 1986.

Hendrick et al., *Mag. Res. Imaging*, 2:193-204, 1984.

Henkelman et al., *J. Magn. Reson. Imaging*, 2:533-540, 1992.

Henkelman and Bronskill, *Rex. Magn. Reson. Med.*, 2(1):1-126, 1987.

Hennig et al., *Magn. Reson. Med.*, 3:823-833, 1986.

Hutchinson and Raff, *Magn. Reson. Med.*, 6:87-91, 1998.

Ikeda et al., *Plast. Reconstr. Surg.*, 104(7):2054-2062, 1999.

Jakob et al., In: *Cardiac imaging with SMASH*, Proc. ISMRM 6th Ann. Mtg., Sydney, 16, 1998.

Jakob et al., In: *AUTO-SMASH, a self-calibrating technique for SMASH imaging*, Proc. ISMRM 6th Ann. Mtg., Sydney, 1975, 1998.

Johnson et al., *Am. J. Roentgenol*, 4(10):13-26, 1983.

Joseph, *J. Comput. Assist. Tomogr.*, 9:651-658, 1985.

Judge and Bryanston-Cross, *Optics Lasers Eng.*, 21:199-239, 1994.

Keller et al., *Radiology*, 164:539-541, 1987.

Kelton et al., In: *An algorithm for rapid image acquisition using multiple receiver coils*, Proc. SMRM 8th Ann. Mtg., Amsterdam, 1172, 1989.

Kuroda et al., *Magn. Reson. Med.*, 40:505-510, 1998.

Kurtz and Dwyer, *J. Comput. Assist. Tomogr.*, 8(8):19-28, 1984.

Kwiat and Einav, *Med. Phys.*, 18:251-265, 1991.

Lauterbur, *Nature*, 242:190-191, 1973.

Li et al., *Radiology*, 153(P)85, 1984.

Liang and Lauterbur, In: *Principles of magnetic resonance imaging: a signal processing approach*, NY, IEEE Press, 2000.

Lodes et al., *J. Comput. Assist. Tomogr.*, 13:85-361, 1989.

Ma, In: *Multipoint Dixon imaging with reduced time and increased reliability*, Proc. $6^{th}$ Ann. Mtg. ISMRM, Sydney, 622, 1998.

Ma et al., *Magn. Reson. Med.*, 48(6):1021-1027, 2002.

Ma et al., In: *Multipoint Dixon Imaging using Sensitivity Encoding*, Proc. Intl. Soc. Magnetic Resonance in Resonance in Medicine, Toronto, Canada, 2003.

Mallard, *BJ Radiol.*, 54:831-849, 1982.

Margosian et al., In: *Partial Fourier acquisition in MRI*, Grant and Harris (Eds.), John Wiley and Sons, 3462-3467, 1996.

Maudsley et al., *J. Magn. Reson.*, 51:147-152, 1983.

Meaney, *J. Comput. Assist. Tomogr.*, 7:768-774, 1983.

Meaney, In: *Scientific program and book of abstracts*, Soc. Magn. Resonance in Medicine, $3^{rd}$ Ann. Mtg., NY/Berkeley, Calif., Society of Magnetic Resonance in Medicine, 322, 1984.

Melki et al., *J. Magn. Reson. Imaging*, 1:319-326, 1991.

Mitchell et al., *Radiology*, 185:345-351, 1992.

Mitchell, *Radiology*, 1851-1861, 1992.

Mitchell and Vinitski, *Radiology*, 178:67-71, 1991.

Mukundan, Jr. et al., *J. Magn. Reson. Imaging*, 3(5):713-717, 1993.

Murakami et al., *Magn. Reson. Imaging*, 35:585-590, 1996.

Noll et al., *IEEE Trans. Med. Imaging*, 10:154-163, 1991.

Paltiel, In: *Separate water and lipids images obtained by a single scan*, Proc. $4^{th}$ Annl. Scientific Mtg. Society of Magnetic Resonance in Medicine, NY Soc. Magnetic Resonance in Medicine, 172-173, 1985.

Patrick et al., In: *Water/fat separation and chemical shift Artifact correction using a single scan*, Proc. $4^{th}$ Ann. Mtg. Soc. Magnetic Resonance in Medicine, NY Society of Magnetic Resonance in Medicine, 174-175, 1985.

Pfleiderer et al., *Magn. Reson. Med.*, 29(5):656-659, 1993.

Proctor and Yu, *Phys. Rev.*, 77:717, 1950.

Pruessmann et al., In: *Spiral SENSE: sensitivity encoding with arbitrary k-space trajectories*, Proc. ISMRM 7th Ann. Mtg., Philadelphia, 94, 1999.
Pruessmann et al., *Magn. Reson. Med.*, 42:952-962, 1999.
Pruessmann et al., In: *Coil sensitivity encoding for fast MRI*, Proc. ISMRM 6th Ann. Mtg., Sydney, 579, 1998.
Pruessmann et al., In: *Coil sensitivity maps for sensitivity encoding and intensity correction*, Proc. ISMRM 6th Ann. Mtg., Sydney, 2087, 1998.
Pykett and Rosen, *Radiology*, 149:197-201, 1983.
Ra and Rim, In: *Fast imaging method using multiple receiver coils with subencoding data set*, Proc. SMRM 10th Ann. Mtg., San Francisco, 1240, 1991.
Ra and Rim, *Magn. Reson. Med.*, 30:142-145, 1993.
Rick et al., *Magn. Reson. Med.*, 30:724-731, 1993.
Roemer et al., *Magn. Reson. Med.*, 16:192-225, 1990.
Rosen et al., *Radiology*, 169:799-804, 1988.
Runge et al., *Am. J. Roentgenol*, 143:1015-1026, 1984.
Rybicki et al., *Am. J. Neuroradiol.*, 22(9):1798-1802, 2001.
Schneider and Chan, *Radiology*, 187(1):89-93, 1993.
Sepponen et al., *J. Comput. Assist. Tomogr.*, 8:585-587, 1984.
Slinner and Glover, *Magn. Reson. Med.*, 37:628-630, 1997.
Smith et al., *Radiology*, 7:954-959, 1983.
Sodickson et al., *Magn. Reson. Med.*, 38:591-603, 1997.
Szumowski et al., *Radiology*, 192:555-561, 1994.
Szumowski et al., *Magn. Reson. Med.*, 34:120-124, 1995.
Tien, *Am. J. Roentgenol*, 158:369-379, 1992.
Twieg et al., *Magn. Reson. Med.*, 5:32-46, 1987.
Wehrli et al., *J. Comput. Assist. Tomogr.*, 8:369-380, 1984.
Weiger et al., In: *Accelerated cardiac breathhold imaging using coil sensitivity encoding*, Proc. ISMRM $6^{th}$ Ann. Mtg., Sydney, 799, 1998.
Weiger et al., In: *Cardiac real-time acquisition using coil sensitivity encoding*, Proc. ISMRM 6th Ann. Mtg., Sydney, 803, 1998.
Williams, *Radiology*, 173:249-253, 1989.
Williams et al., In: *Gray's anatomy*, 37th ed. NY; Churchill-Livingstone, 1989.
Xiang and Henkleman, *J. Magn. Reson. Imaging*, 1:633-642, 1991.
Xiang et al., In: *Phase correction in two-point Dixon chemical shift imaging*, Proc. $3^{rd}$ Ann. Scientific Mtg. Soc. Magn. Resonance, Nice: Society of Magnetic Resonance, 1904, 1995.
Xiang and An, In: *General 3-point water-fat imaging with optimized SNR*, Proc. $4^{th}$ Ann. Scientific Mtg. Intl. Soc. Magnetic Resonance in Medicine, NY Intl. Soc. Magn. Resonance in Medicine, 1544, 1996.
Xiang and An, In: *Water-fat imaging with direct phase encoding*. Proc. $3^{rd}$ Ann. Scientific Ann. Mtg. Soc. Magn. Resonance, Nice: Society of Magnetic Resonance, 658, 1995.
Xiang and Henkelman, *Magn. Reson. Med.*, 29:422-428, 1993.
Xiang et al., *J. Magn. Reson. Imaging*, 3:900-906, 1993.
Xiang and An, *J. Magn. Reson. Imaging*, 7(6):1002-1015, 1997.
Yang et al., In: *BO inhomogeneity correction for two point Dixon chemical shift imaging*, Proc. $11^{th}$ Ann. Scientific Mtg. Soc. Magn. Resonance in Medicine, Berlin Soc. Magnetic Resonance in Medicine, 3819, 1992.
Yeung et al., *Radiology*, 167:537-540, 1988.
Yeung and Kormos, *Radiology*, 159:783-786, 1986.
Young et al., *Mag. Res. Med.*, 2:81-85, 1985.
Young, *Br. Med. Bull.*, 40:139-147, 1984.
Zhu et al., In: *A robust water and fat separation method*, Proc. $4^{th}$ Ann. Scientific Mtg. Soc. Magn. Resonance, NY Soc. Magnetic Resonance, 1542, 1996.
Zimmerman, In: *MRI in intracranial meningiomas*, Proc. $3^{rd}$ Ann. Mtg. Society of Magnetic NY/Berkeley, Calif., Society of Magnetic Resonance in Medicine, 779, 1984.

The invention claimed is:

1. A method for chemical shift imaging comprising:
   obtaining a plurality of magnetic resonance imaging data signals using a Dixon technique combined, with an inversion recovery technique; and
   processing the plurality of magnetic resonance imaging data signals using a Dixon reconstruction technique to create a chemical shift image.

2. The method of claim 1, the data signals comprising signals for a plurality of chemical species.

3. The method of claim 2, the plurality of chemical species comprising water, fat, and silicon.

4. The method of claim 1, the inversion recovery technique comprising a short tau inversion recovery technique.

5. The method of claim 1, further comprising selecting an inversion time appropriate for suppressing a chemical species based on the relaxation time constant of the chemical species.

6. The method of claim 1, the Dixon technique comprising a spin echo technique.

7. The method of claim 6, the spin echo technique comprising a fast spin echo technique.

8. The method of claim 1, the Dixon technique comprising a gradient echo technique.

9. The method of claim 1, the Dixon technique comprising a two-point Dixon technique.

10. The method of claim 1, the Dixon technique comprising a three-point Dixon technique.

11. The method of claim 1, the Dixon technique comprising a fast Dixon technique.

12. The method of claim 11, the fast Dixon technique further comprising:
    generating an echo shifting gradient pulse on a readout axis in the presence of a primary and gradient magnetic field system;
    generating a readout gradient pulse on the readout axis; and
    detecting magnetic resonance echo signals resulting from the readout gradient.

13. The method of claim 12, further comprising generating a compensating gradient pulse on the readout axis.

14. The method of claim 13, the compensating gradient pulse having a polarity opposite a polarity of the echo shifting gradient pulse.

15. The method of claim 1, the Dixon reconstruction technique comprising a Dixon phase-correction scheme.

16. The method of claim 15, the Dixon phase-correction scheme comprising:
    selecting an orientation vector parallel to a direction of local field inhomogeneity of the plurality of magnetic resonance imaging data signals; and
    correcting phase errors of the plurality of magnetic resonance imaging data signals using the orientation vector.

17. The method of claim 1, the Dixon reconstruction technique comprising a sensitivity encoding reconstruction technique.

18. The method of claim 1, the step of obtaining the plurality of magnetic resonance imaging data signals using a Dixon technique combined with the inversion recovery technique suppresses a plurality of signals for one chemical species from the data signals.

19. The method of claim 18, the chemical species comprising fat.

20. The method of claim 1, the step of obtaining a plurality of magnetic resonance imaging data signals further comprising using a sensitivity encoding technique.

21. The method of claim 1, wherein images of two different chemical species are produced.

22. The method of claim 21, wherein the two chemical species are water and silicone.

23. An apparatus to produce a chemical shift image comprising:
a magnetic resonance imaging scanner for obtaining images;
a controller configured to provide input to the scanner to acquire images using a Dixon technique combined with a short tau inversion recovery technique to produce a plurality of magnetic resonance imaging data signals, and processing the plurality of magnetic resonance imaging data signals using a Dixon reconstruction technique to create a chemical shift image; and
an output device to display the resulting image.

24. The apparatus of claim 23, the Dixon technique comprising a fast spin echo technique.

25. The apparatus of claim 24, the fast Dixon technique further comprising:
generating an echo shifting gradient pulse on a readout axis in the presence of a primary and gradient magnetic field system;
generating a readout gradient pulse on the readout axis; and
detecting magnetic resonance echo signals resulting from the readout gradient.

26. The apparatus of claim 25, the controller further generating a compensating gradient pulse on the readout axis.

27. The apparatus of claim 26, the compensating gradient pulse comprising a polarity opposite a polarity of the echo shifting gradient pulse.

28. The apparatus of claim 23, the Dixon technique comprising a fast Dixon technique.

29. The apparatus of claim 23, the Dixon reconstruction technique including a Dixon phase-correction scheme.

30. The apparatus of claim 29, wherein the Dixon phase-correction scheme comprises:
selecting an orientation vector parallel to a direction of local field inhomogeneity of the plurality of magnetic resonance imaging data signals; and
correcting phase errors of the plurality of magnetic resonance imaging data signals using the orientation vector.

31. The apparatus of claim 23, the controller using the Dixon reconstruction technique including a sensitivity encoding reconstruction technique that preserves the relative phase information for each Dixon image.

32. The apparatus of claim 23, the controller using the short tau inversion recovery technique to suppress a plurality of fat signals from the plurality of magnetic resonance imaging data signals.

33. The apparatus of claim 23, the controller being further configured to calculate a water-only image and a silicone-only image.

* * * * *